United States Patent
Magidson

(10) Patent No.: US 6,745,397 B2
(45) Date of Patent: Jun. 8, 2004

(54) EYE SHADE

(76) Inventor: Shirley Magidson, 4671 Leaby St., Culver City, CA (US) 90232

( * ) Notice: Subject to any disclaimer, the term of this patent is extended or adjusted under 35 U.S.C. 154(b) by 0 days.

(21) Appl. No.: 10/001,698

(22) Filed: Oct. 31, 2001

(65) Prior Publication Data

US 2003/0079266 A1 May 1, 2003

(51) Int. Cl.$^7$ .................................................. A61F 9/00
(52) U.S. Cl. ......................................... 2/15; 2/15
(58) Field of Search .................. 2/15, 9, 426; 128/857, 128/858; 602/74

(56) References Cited

U.S. PATENT DOCUMENTS

| | | | | |
|---|---|---|---|---|
| 854,546 A | * | 5/1907 | Verdeau | 2/206 |
| 1,743,801 A | * | 1/1930 | Reynolds | 2/15 |
| 2,891,252 A | * | 6/1959 | Lazo | 2/15 |
| 3,952,331 A | * | 4/1976 | Melville | 2/431 |
| 5,661,850 A | * | 9/1997 | Martinique | 2/15 |
| 6,019,103 A | * | 2/2000 | Carroll | 128/858 |

* cited by examiner

Primary Examiner—John J. Calvert
Assistant Examiner—Katherine Moran
(74) Attorney, Agent, or Firm—Blakely Sokoloff Taylor & Zafman

(57) ABSTRACT

An eye shade is presented including a first side connected to an intermediate layer. A second side is connected to the intermediate layer. A first outer eye portion and a second outer eye portion are formed from the first side, the intermediate layer and the second side. The first and second outer eye portions extend outward. The first outer eye portion and the second outer eye portion are convex shaped.

17 Claims, 10 Drawing Sheets

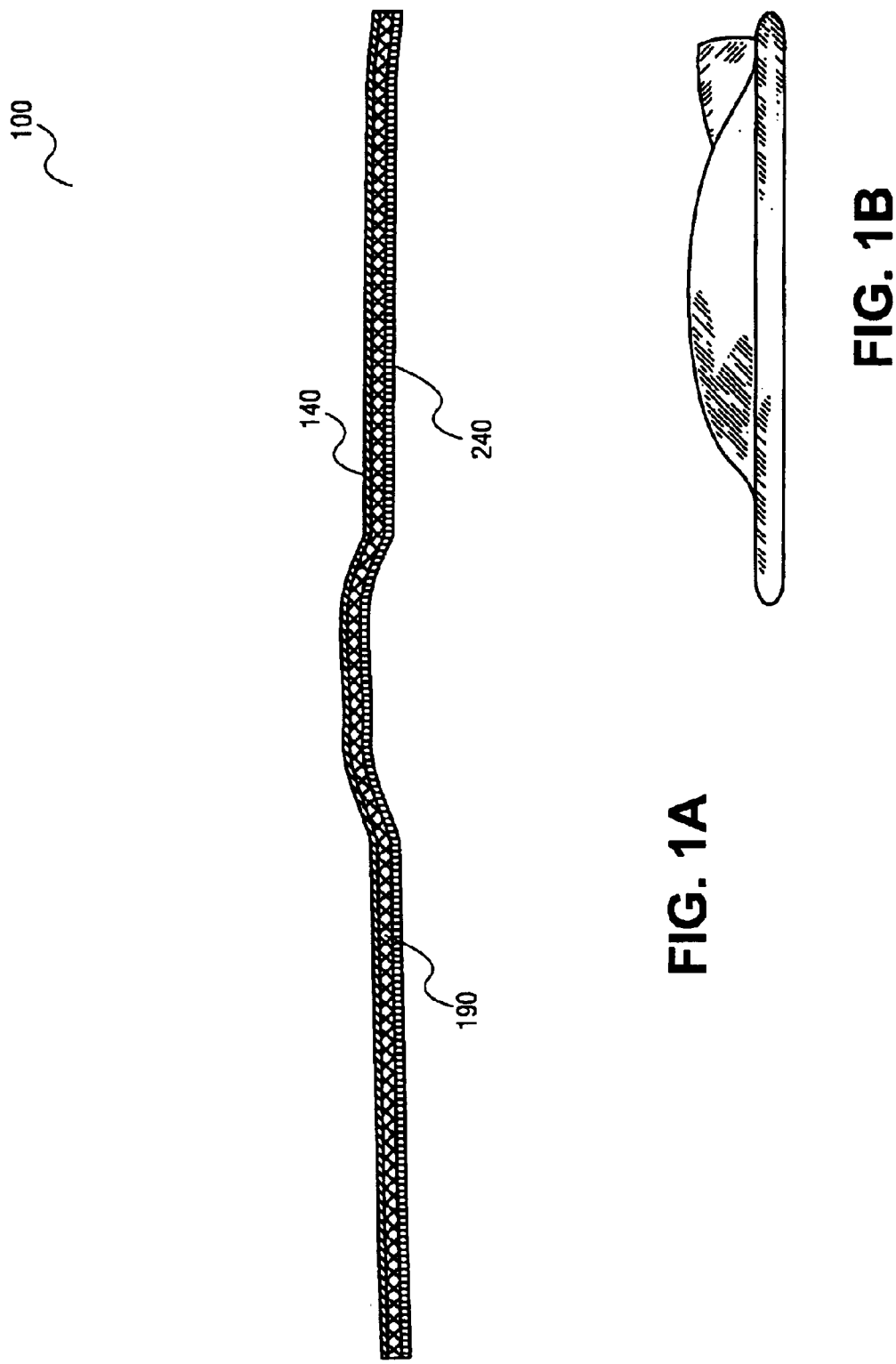

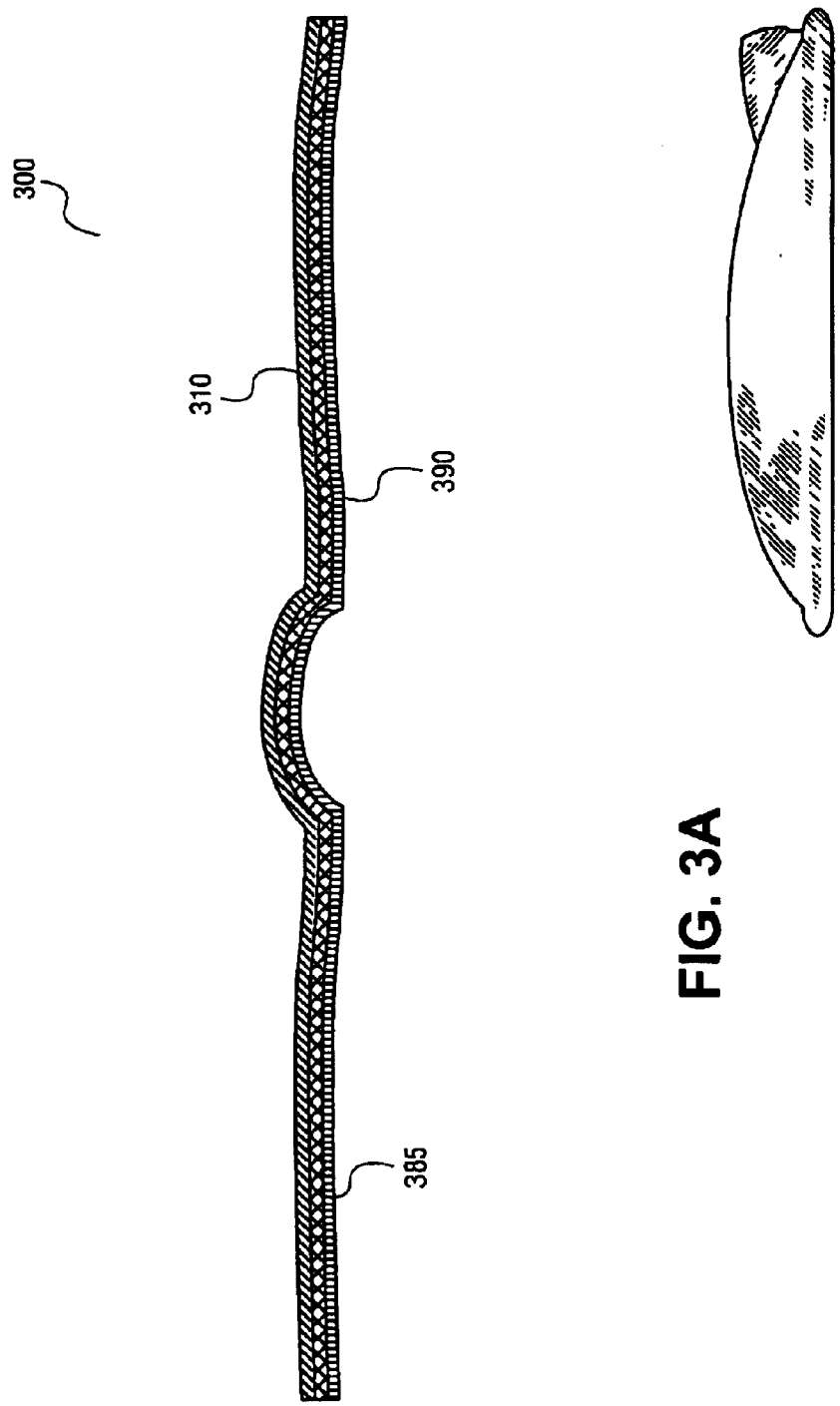

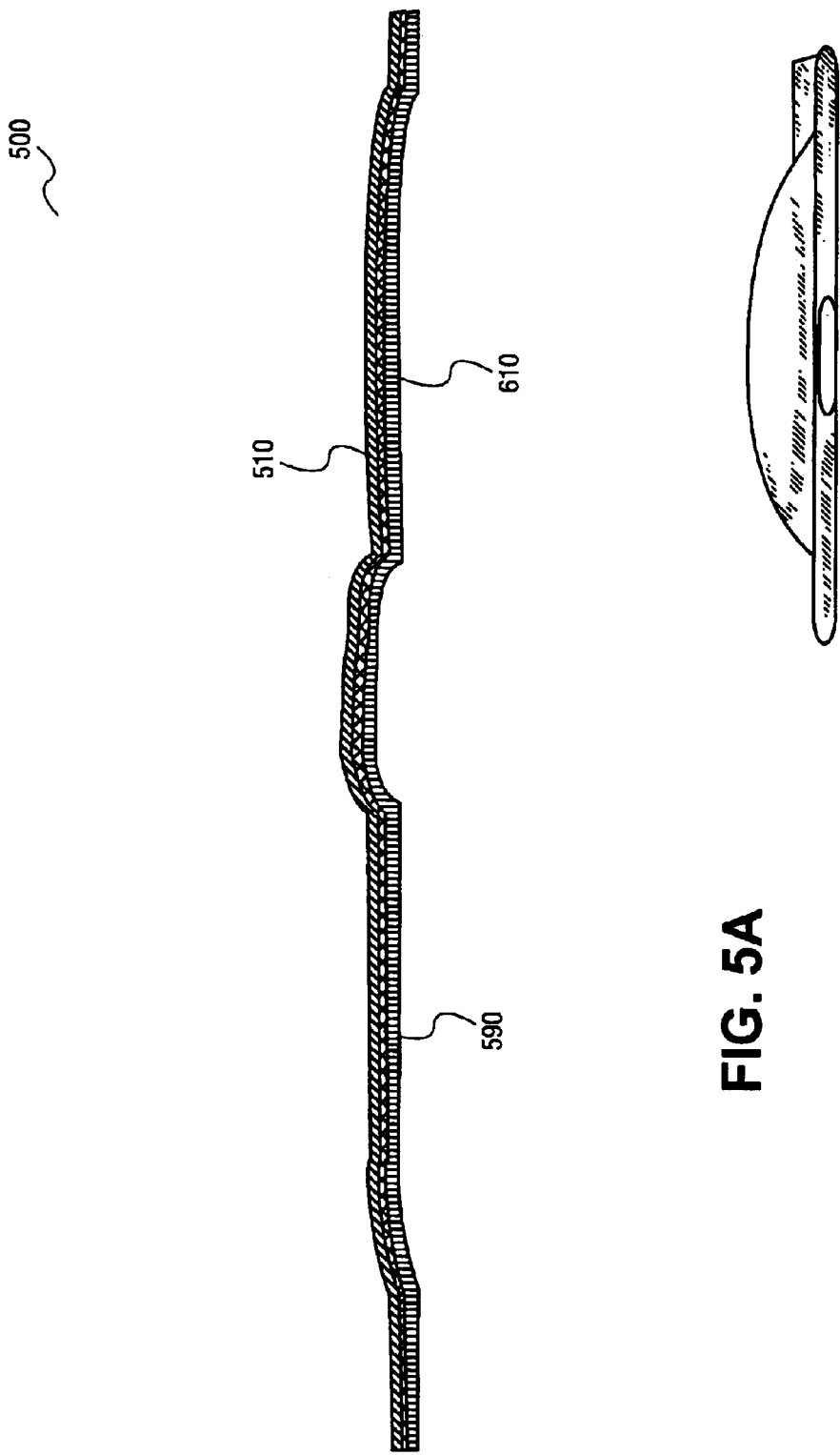

EYE SHADE

BACKGROUND OF THE INVENTION

1. Field of the Invention

This invention relates to eye shades, and more particularly to an eye shade designed to exclude light rays from the eyes without contacting a person's eyes or eyelashes.

2. Description of the Related Art

There are many eye shades on the market today to assist people to get a restful sleep by occluding light rays. Eye shades can be used in many places and for many reasons. The existing eye shades, however, have some limitations. One of these limitations is that the existing eye shades do not permit users to open their eyes while wearing the eye shade without having a portion of the eye shade touch either a user's eye or eye lashes. Another limitation is that an eye shade user may have applied eye makeup that can be smudged or altered by coming into contact with an eye shade while it is being worn. Since eye shades may be used for purposes other than sleep, permitting the wearer to open one's eyes affects comfort. Moreover, a person with very long eyelashes, or enhanced eyelashes, may experience a very uncomfortable feeling wearing an eye shade, which interferes with blinking of his or her eyes.

SUMMARY

An eye shade is presented having a first side coupled to an intermediate layer. A second side is coupled to the intermediate layer. A first outer eye portion and a second outer eye portion are formed from the first side, the intermediate layer and the second side. The first and second outer eye portions extend outward. The first outer eye portion and the second outer eye portion are convex shaped. A user wearing the eye shade over their eyes avoids contact with the inner eye portions even if the person had long or enhanced eyelashes.

Also presented is an eye shade including a first side connected to an intermediate layer. A second side is connected to the intermediate layer. A first inner eye portion and a second inner eye portion are formed from the first side, the intermediate layer and the second side. The first and second inner eye portions extend inward. The first inner eye portion and the second inner eye portion are concave shaped. A user wearing the eye shade over their eyes avoids contact with the inner eye portions even if the person had long or enhanced eye lashes.

BRIEF DESCRIPTION OF THE DRAWINGS

The invention is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

FIG. 1A illustrates an edge view of the embodiment illustrated in FIG. 1.

FIG. 1B illustrates a side view of an eye portion of the embodiment illustrated in FIG. 1.

FIG. 3A illustrates an edge view of the embodiment illustrated in FIG. 3.

FIG. 3B illustrates a side view of an eye portion of the embodiment illustrated in FIG. 3.

FIG. 5A illustrates an edge view of the embodiment illustrated in FIG. 5.

FIG. 5B illustrates a side view of an eye portion of the embodiment illustrated in FIG. 5.

DETAILED DESCRIPTION OF THE INVENTION

The invention generally relates to an eye shade. Referring to the figures, exemplary embodiments of the invention will now be described. The exemplary embodiments are provided to illustrate the invention and should not be construed as limiting the scope of the invention.

Figure 1:
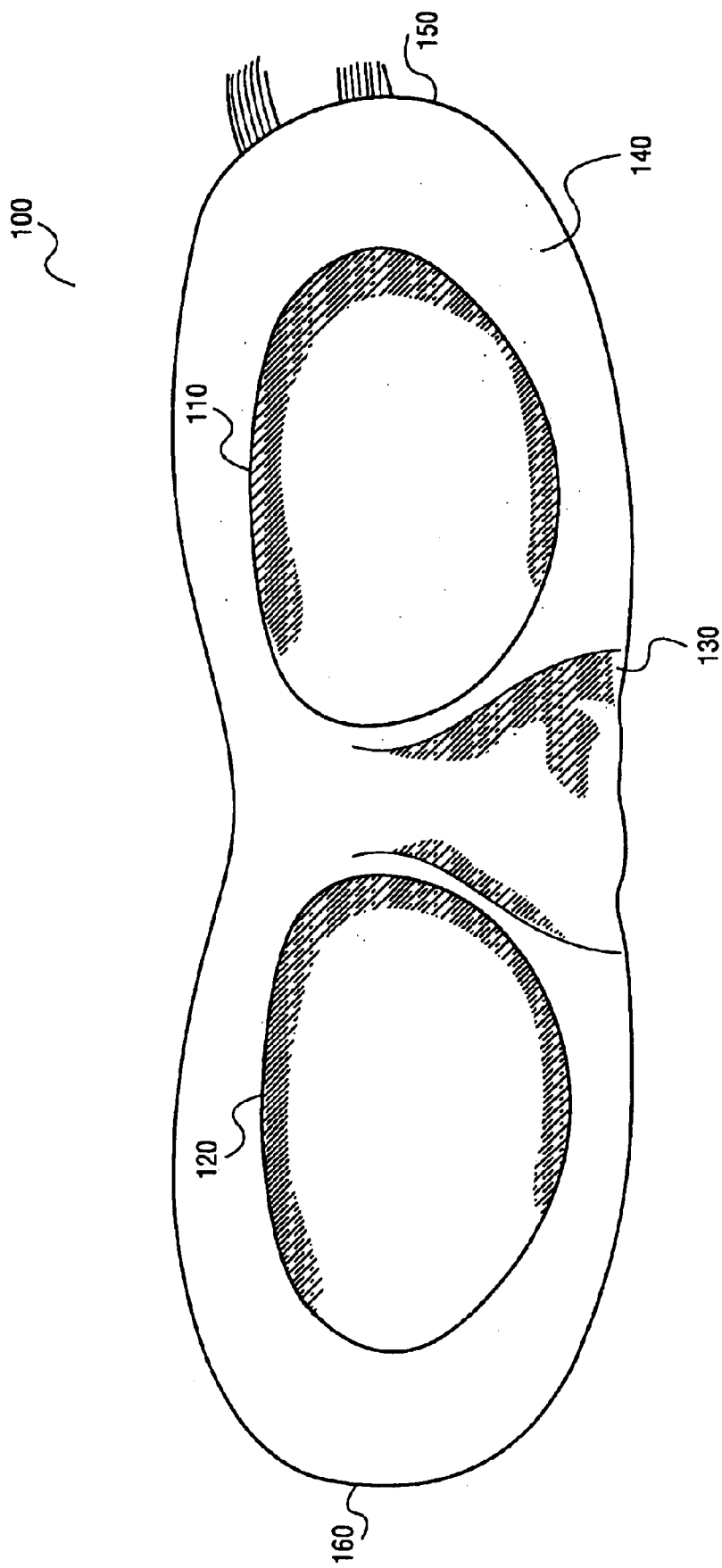
FIG. 1 illustrates a front view of an embodiment of the invention having outer convex shaped eye portions extending away from a front portion.

FIG. 1 illustrates a front view of an embodiment of the invention. In this embodiment of the invention, eye shade 100 comprises left outer eye portion 110, right outer eye portion 120, outer nose portion 130 and front portion 140. Left outer eye portion 110, and right outer eye portion 120 are convex in shape extending away from front portion 140. Outer nose portion 130 is convex in shape extending away from front portion 140.

Figure 2:
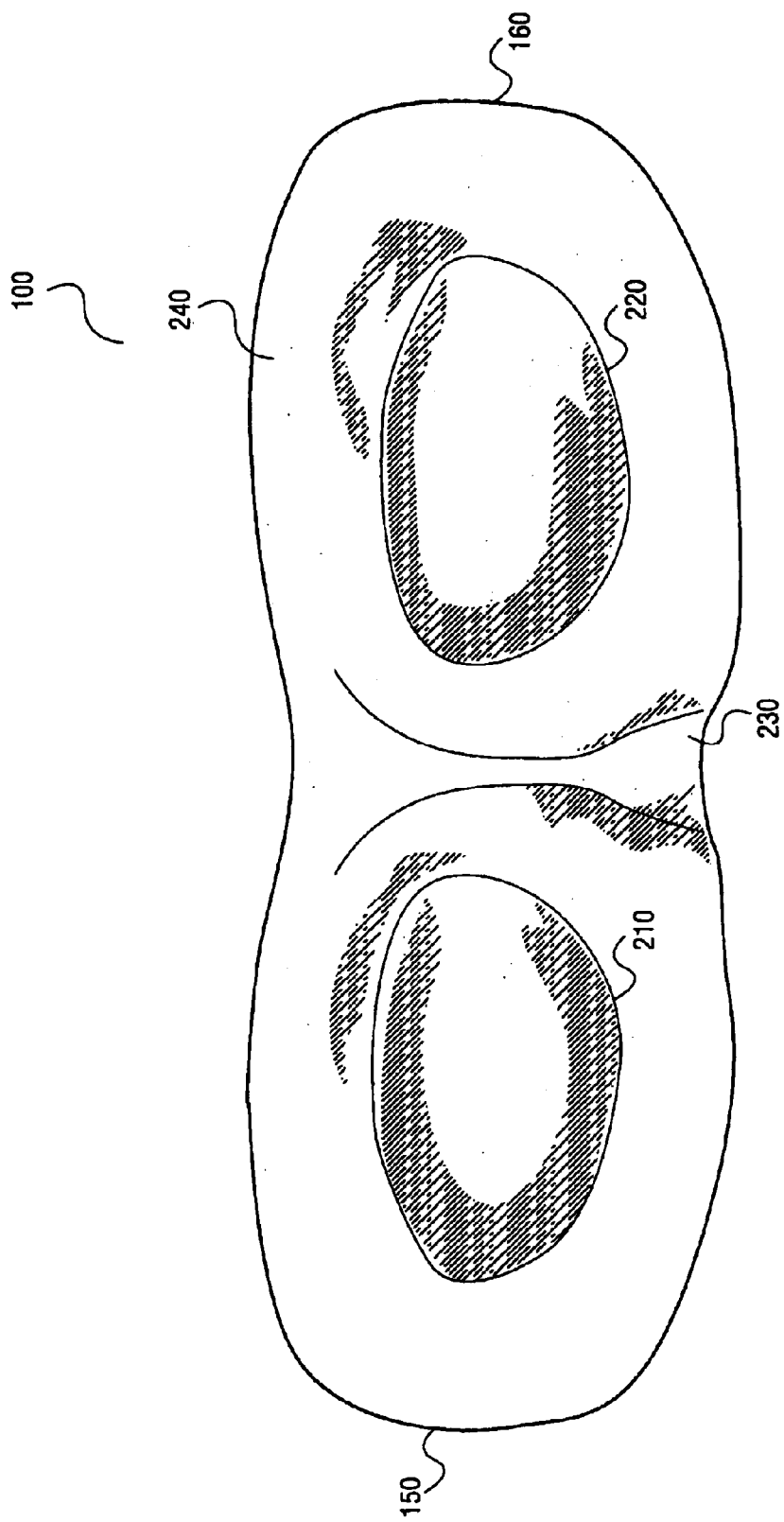
FIG. 2 illustrates a rear view of the embodiment illustrated in FIG. 1.
Figure 2A:
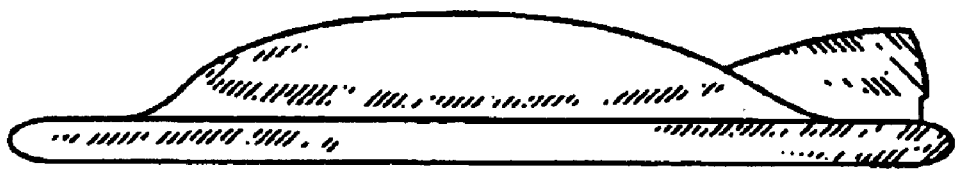

FIG. 2 illustrates the rear view of eye shade 100. Left inner eye portion 210 is the inner compliment to left outer eye portion 110. Right inner eye portion 220 is the compliment to right outer portion 120. Left inner eye portion 210 and right inner eye portion 220 are both concave shaped. Rear portion 240 is the compliment to front portion 140. Inner nose portion 230 is the compliment to outer nose portion 130. Inner nose portion 230 is concave in shape.

Left inner eye portion 210 and right inner eye portion 220 can vary in length, width and depth dimensions to prevent various sized eyelashes and eye portions of users from coming into contact with the surface of either left inner eye portion 210 or right inner eye portion 220. FIG. 1B illustrates a side view of an eye portion of the embodiment illustrated in FIG. 1. Only one eye portion is illustrated as the left and right eye portions are symmetrical The depth h (illustrated in FIG. 1B) of either left inner eye portion 210 or right inner eye portion 220 can be a depth in the range of three-fourths (¾) of an inch to three and a half (3½) inches at the center of either inner left eye portion 210 or inner right eye portion 220. That is, different embodiments can have different depth h to accommodate various length eye lashes or enhanced eyelashes (such as false or fake eyelashes). Eye shade 100 can vary in dimension so as to accommodate various facial shapes and sizes.

Eye shade 100 can have both front portion 140 and rear portion 240 comprised of suitable man-made material that can be formed over an inner portion lying between front portion 140 and rear portion 240 that is comprised of suitable compressible material, such as a foam rubber type material. The composition of front portion 140, rear portion 240 and inner portion 190 (illustrated in FIG. 1A) lying between front portion 140 and rear portion 240 are such that eye shade 100 can be formed by a heat source in a press which molds the composite materials. Since eye shade 100 is comprised of molded material, eye shade 100 has "memory." Therefore, eye shade 100 can be folded, twisted, washed, etc., and will retain its formed shape.

Eye shade 100 can have varying means for positioning on or attaching to a face. Such means include a single strap, a plurality of coupled straps, etc. These positioning/attaching means can be made of a single elastic piece attached to right end side 160 and left end side 150, or separate pieces wherein complimentary pieces are each coupled to right end 160 and left end 150. For embodiments of eye shade 100 having a plurality of positioning/attaching pieces, various means can be used for fastening each of the plurality of pieces together. These means include, VELCRO® hook and loop fasteners, metal connectors, plastic connectors, buckles, snaps, etc. The positioning pieces can be adjustable and also vary in length and width, to accommodate various sized users.

In this embodiment the nose portion, comprising outer nose portion 130 and inner nose portion 230, can be varied in size to accommodate various sized noses. In another embodiment of the invention, the nose portion can be partially or entirely removed.

Figure 3:
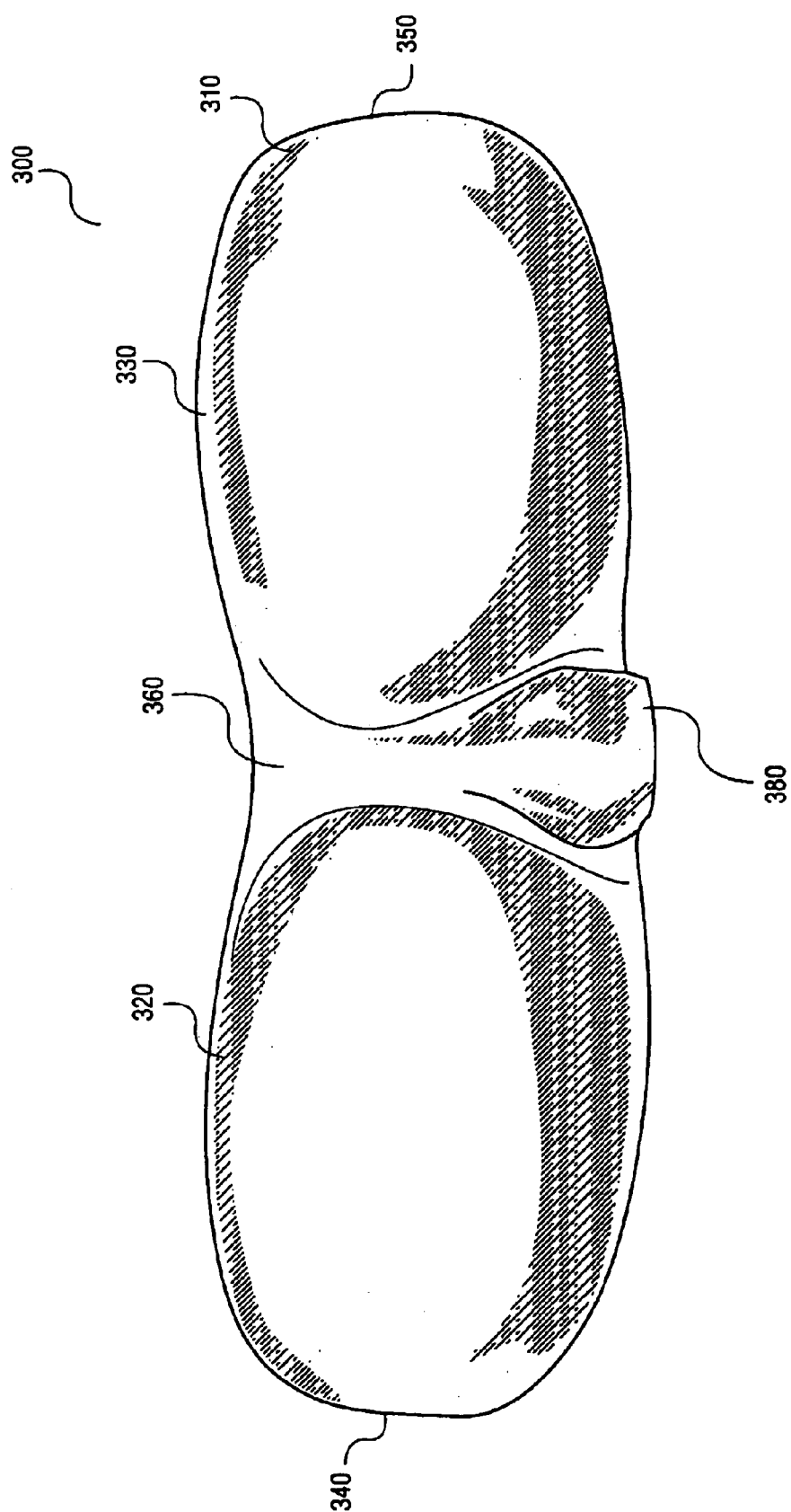
FIG. 3 illustrates a front view of another embodiment of the invention having inner concave shaped eye portions extending away from a rear portion.

FIG. 3 illustrates a front view of another embodiment of the invention. Eye shade 300 is comprised of left outer eye portion 330, right outer eye portion 320, front portion 310, left end 350, right end 340, outer nose portion 380 and bridging portion 360. Left outer eye portion 330 and right eye outer eye portion 320 are can be flat or slightly convex in shape extending outward slightly from bridging portion 360. Left outer eye portion 330 and right outer eye portion 320 comprise most of eye shade 300 with the exception of outer nose portion 380 and bridging portion 360. In another embodiment of the invention, left outer eye portion 330 and right outer eye portion 320 are combined to form a single outer portion (not shown). In this embodiment of the invention, eye shade 300 does not have left and right outer eye portions that are separately distinguishable.

Figure 4:
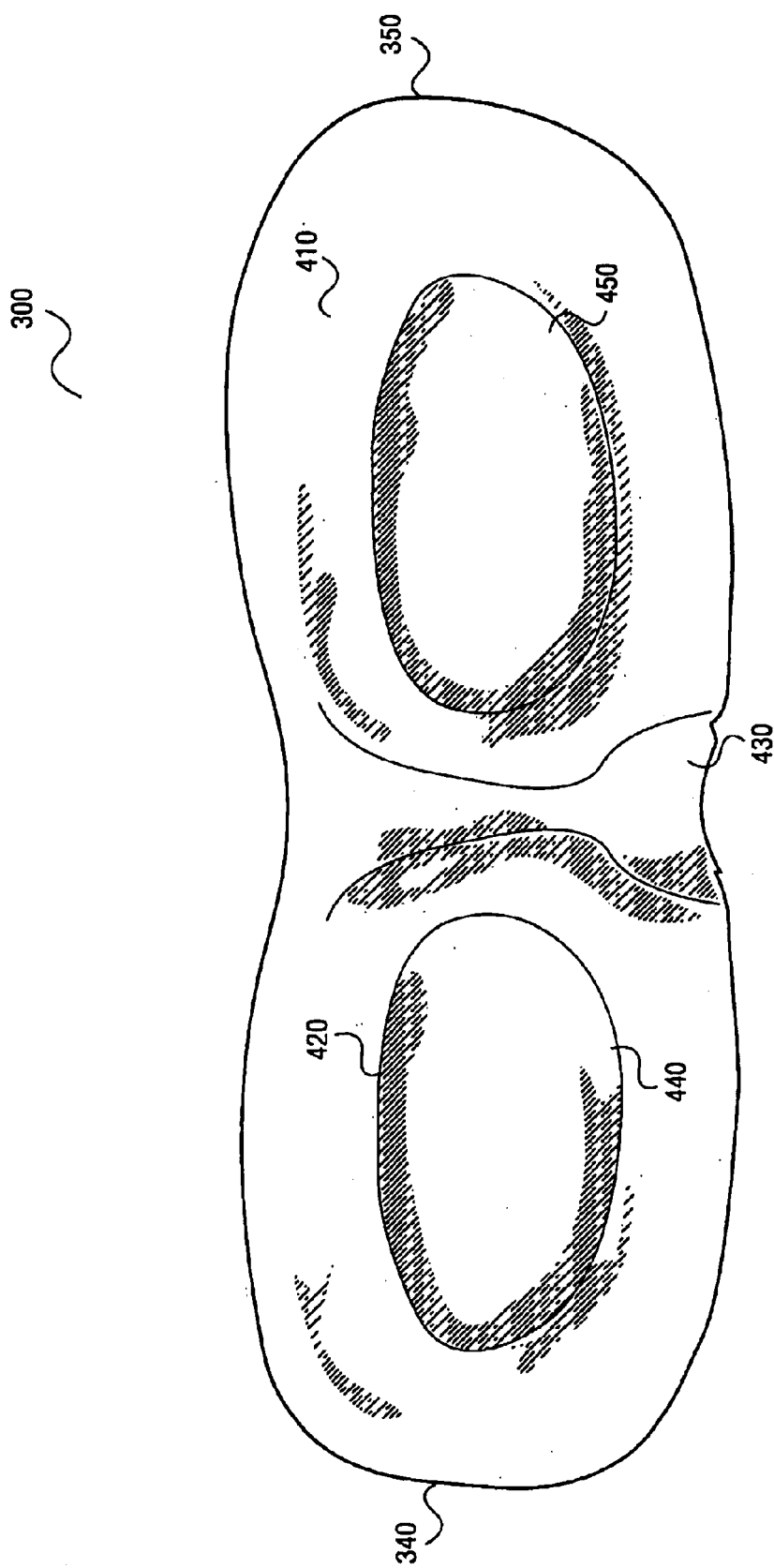
FIG. 4 illustrates a rear view of the embodiment illustrated in FIG. 3.

FIG. 4 illustrates a rear view of eye shade 300, Left inner eye portion 420 surrounds left inner eye cavity portion 440. Right inner eye portion 410 surrounds right eye cavity 450. Left inner eye cavity 440 and right inner eye cavity 450 are concave in shape. Inner nose portion 430 is concave in shape. When eye shade 300 is placed over a user's eyes, left inner eye cavity 440 and right inner eye cavity 450 are not brought into contact with a user's eyelashes or eye portions. Left inner eye cavity 440 and right inner eye cavity 450 can be formed with varying dimensions to allow a person with long eyelashes or enhanced eyelashes (i.e., false or fake eyelashes, from coming into contact with the surface of eye shade 300. FIG. 3B illustrates a side view of an eye portion of the embodiment illustrated in FIG. 3. Only one eye portion is illustrated as the left and right eye portions are symmetrical. The depth h (illustrated in FIG. 3B) of either left inner eye cavity 440 or right inner eye cavity 450 can be a depth in the range of three-fourths (¾) of an inch to three and a half (3½) inches at the center of either inner left eye cavity 440 or inner right eye cavity 450. That is, different embodiments can have different depth h to accommodate various length eye lashes or enhanced eyelashes (such as false or fake eyelashes). Eye shade 300 can vary in dimension so as to accommodate various facial shapes and sizes.

Eye shade 300 can have varying means for positioning on or attaching to a face. Such means include a single strap, a plurality of coupled straps, etc. These positioning/attaching means can be made of a single elastic piece attached to right end side 340 and left end side 350, or separate pieces wherein complimentary pieces are each coupled to right end side 340 and left end side 350. For embodiments having a plurality of positioning/attaching pieces, various means can be used for fastening each of the plurality of pieces together. These means include, VELCRO® hook and loop fasteners, metal connectors, plastic connectors, buckles, snaps, etc. The positioning pieces can be adjustable and also vary in length and width, to accommodate various sized users.

In this embodiment the nose portion, comprising outer nose portion 330 and inner nose portion 430, can be varied in size to accommodate various sized noses. Also, the nose portion can be partially or entirely removed without affecting the scope of this embodiment.

Figure 5:
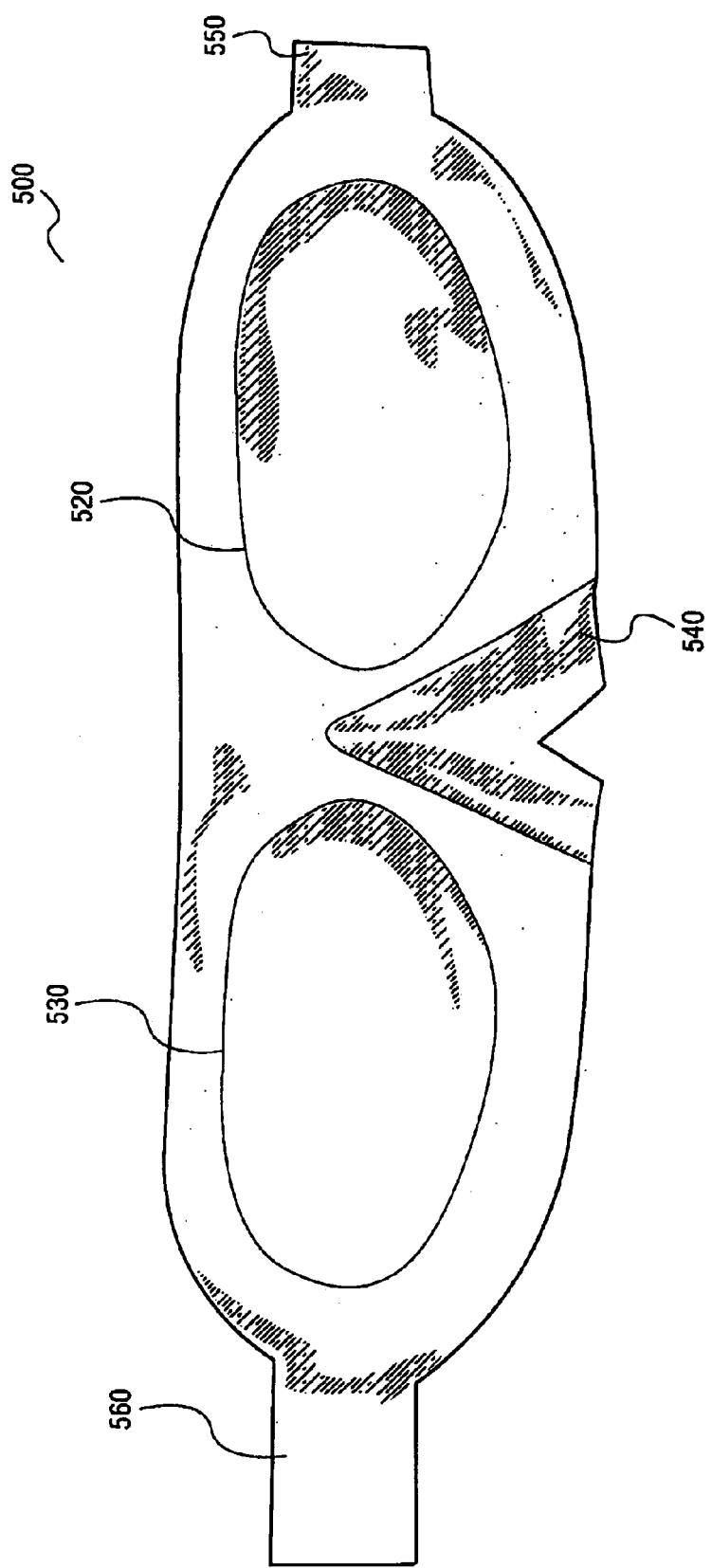
FIG. 5 illustrates a front view of still another embodiment of the invention having outer convex shaped eye portions extending away from a front portion and a symmetrical front portion.

FIG. 5 illustrates a front view of still another embodiment of the invention. Eye shade 500 is comprised of front portion 510, left outer eye portion 520, right outer eye portion 530, outer nose portion 540, left side portion 550, and right side portion 560. Left outer eye portion 520 and right outer eye portion 530 are convex in shape extending away from front portion 510. Outer nose portion 540 is triangular shaped and polygonal in dimension. Outer nose portion 540, however, is not necessarily restricted to such a shape, and for example, may be circular, elliptical, oval, triangular with rounded angles, trapezoidal, diamond shaped, heart-shaped, etc. Eye shade 500 has a linear upper circumferential portion.

Figure 6:
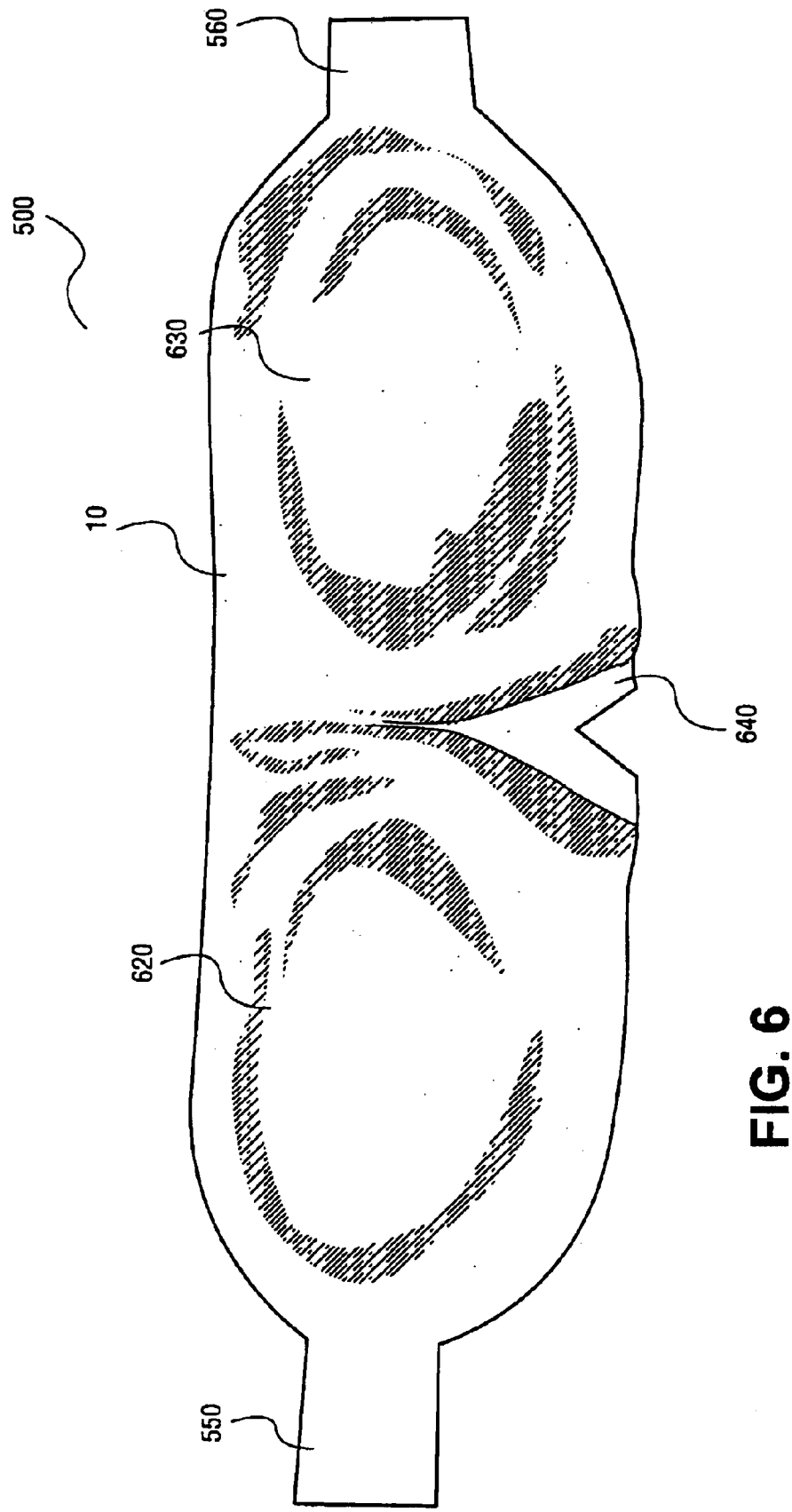
FIG. 6 illustrates a rear view of the embodiment illustrated in FIG. 5.

FIG. 6 illustrates a rear view of eye shade 500. Left inner eye portion 620 and right inner eye portion 630 are concave in shape. Left inner eye portion 620 and right inner eye portion 630 can have variable dimensions to allow for varying lengths of eye portions (i.e., eyeball, upper and lower eyelids, eyebrow), eyelashes and additional eyelash enhancements (i.e., false or fake eyelashes) that can be added to a person's upper or lower eye lids, without such lashes or enhancements coming into contact with the inner surface of either left inner eye portion 620 or right inner eye portion 630. FIG. 5B illustrates a side view of an eye portion of the embodiment illustrated in FIG. 5. Only one eye portion is illustrated as the left and right eye portions are symmetrical The depth h (illustrated in FIG. 5B) of either left inner eye portion 620 or right inner eye portion 630 can be a depth in the range of three-fourths (¾) of an inch to three and a half (3½) inches at the center of either inner left eye portion 620 or inner right eye portion 630. That is, different embodiments can have different depth h to accommodate various length eye lashes or enhanced eyelashes (such as false or fake eyelashes).

Eye shade 500 can have both front portion 510 and rear portion 610 comprised of suitable man-made material that can be formed over inner portion 590 (illustrated in FIG. 5A) lying between front portion 510 and rear portion 610 that is comprised of suitable compressible material, such as a foam rubber type material. The composition of front portion 510, rear portion 610 and inner portion 590 lying between front portion 510 and rear portion 610 is such that eye shade 500 can be formed by a heat source in a press which molds the composite materials. Since eye shade 500 is comprised of molded material, eye shade 500 has "memory." Therefore, eye shade 500 can be folded, twisted, washed, etc., and will retain its formed shape.

Eye shade 500 can have varying means for positioning on or attaching to a face. Such means include a single strap, a plurality of coupled straps, etc. These positioning/attaching means can be made of a single elastic piece attached to right side portion 560 and left side portion 550, or separate pieces wherein complimentary pieces are each coupled to right side portion 560 and left side portion 550. For embodiments having a plurality of positioning/attaching pieces, various means can be used for fastening each of the plurality of pieces together. These means include, Velcro, metal connectors, plastic connectors, buckles, snaps, etc. The positioning pieces can be adjustable and also vary in length and width, to accommodate various sized users.

In this embodiment of the invention, the nose portion, comprising outer nose portion 540 and inner nose portion 640, can be varied in size to accommodate various sized noses. Also, the nose portion can be partially or entirely removed.

The forming of eye cavities having suitable dimensions and shapes allow the inventive eye shades to be worn by users without having a user's eye portions (i.e., eyeball, upper and lower eyelids, eyebrow), eye lashes, or eye lash enhancements(i.e., false or fake eyelashes) coming into contact with inner eye portions of the eye shades during use. Also, a user's eye makeup will not be compromised by wearing the various embodiments of the invention as the eye portions of the eye shade embodiments extend beyond the general orbital area (e.g., eye liner extending beyond the orbital extremity area opposite of the nasal area, eye shadow, eyebrow liner). Therefore, a user can open, close, or blink their eyes without coming into contact with an inner eye portion of embodiments of the invention. Moreover, a user wearing enhanced eye lashes, such as very long novelty eye lashes, can use the above mentioned embodiments of the invention without the enhanced eye lashes coming into contact with inner portions.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. An eye shade comprising:
    a first side coupled to an intermediate layer;
    a second side coupled to the intermediate layer;
    a first outer eye portion and a second outer eye portion formed from the first side, the intermediate layer and the second side, and the first and second outer eye portions extend outward,
    a first inner eye portion and a second inner eye portion formed from the first side, the intermediate layer and the second side, the first and second inner eye portions do not come in contact to a user's surrounding eye area to avoid compromising eye makeup, eye makeup including eyebrow, eye liner and eye shadow makeup, and
    a nose portion formed from the first side, the intermediate layer and the second side,
    wherein the first outer eye portion and the second outer eye portion are convex shaped, said first side and said second side are each made from the same type of material, and light cannot pass through said eye shade.

2. The eye shade of claim 1, wherein the first inner eye portion and the second inner eye portion are concave shaped.

3. The eye shade of claim 2, wherein the first inner eye portion and the second inner eye portion have a depth such that a person wearing the eye shade avoids contact with the first and second inner eye portions.

4. The eye shade of claim 2, wherein the first inner eye portion and the second inner eye portion each have a depth range between ¾ and 3½ inches to accommodate one of false and fake eyelashes.

5. The eye shade of claim 1, wherein the first side, the intermediate layer and the second side are coupled together by using a heat source.

6. The eye shade of claim 1, further including means for attaching to a person's face.

7. An eye shade comprising:
    a first side coupled to an intermediate layer;
    a second side coupled to the intermediate layer;
    a first inner eye portion and a second inner eye portion formed from the first side, the intermediate layer and the second side, and the first and second inner eye portions extend inward,
    a first outer eye portion and a second outer eye portion formed from the first side, the intermediate layer and the second side, and
    a nose portion formed from the first side, the intermediate layer and the second side, the first outer portion extending from a left edge of the eye shade to the nose portion, the second outer portion extending from a right edge of the eye shade to the nose portion.
    wherein the first inner eye portion and the second inner eye portion are concave shaped, the first and second inner eye portions do not come in contact with a user's surrounding eye area to avoid compromising eye makeup, said first side and said second side are each made from the same type of material and light cannot pass through said eye shade.

8. The eye shade of claim 7, wherein the first outer eye portion and the second outer eye portion are separate and slightly convex shaped.

9. The eye shade of claim 7, wherein the first inner eye portion and the second inner eye portion have a depth such that a person wearing the eye shade avoids contact with the first and second inner eye portions.

10. The eye shade of claim 7, wherein the first side, the intermediate layer and the second side are coupled together by using a heat source.

11. The eye shade of claim 7, wherein the first inner eye portion and the second inner eye portion each have a depth range between ¾ and 3½ inches to accommodate one of false and fake eyelashes.

12. The eye shade of claim 7, further including means for attaching to a person's face.

13. An eye shade comprising:
    a first side coupled to an intermediate layer;
    an upper linear edge portion, and a bottom edge portion,
    a second side coupled to the intermediate layer;
    a first outer eye portion and a second outer eye portion formed from the first side, the intermediate layer and the second side, and the first and second outer eye portions extend outward;
    a first inner eye portion and a second inner eye portion formed from the first side, the intermediate layer and the second side, and the first and second inner eye portions extend inward, the first and second inner eye portions do not come in contact with a user's surrounding eye area to avoid compromising eye makeup, and
    a nose portion formed from the first side, the intermediate layer and the second side, the first outer portion extending from a left edge of the eye shade to the nose portion, the second outer portion extending from a right edge of the eye shade to the nose portion, wherein the first inner eye portion and the second inner eye portion are concave shaped and the first outer eye portion and the second outer eye portion are convex shaped, said first side and said second side are each made from the same type of material and light cannot pass through said eye shade.

14. The eye shade of claim 13, wherein the first inner eye portion and the second inner eye portion have a depth such that a person wearing the eye shade avoids contact with the first and second inner eye portions.

15. The eye shade of claim 13, wherein the first side, the intermediate layer and the second side are coupled together by using a heat source.

16. The eye shade of claim 13, wherein the first inner eye portion and the second inner eye portion each have a depth range between ¾ and 3½ inches.

17. The eye shade of claim 13, further including means for attaching to a person's face.

* * * * *

UNITED STATES PATENT AND TRADEMARK OFFICE
CERTIFICATE OF CORRECTION

PATENT NO. : 6,745,397 B2  Page 1 of 1
APPLICATION NO. : 10/001698
DATED : June 8, 2004
INVENTOR(S) : Magidson It is certified that error appears in the above-identified patent and that said Letters Patent is hereby corrected as shown below:

Col. 6, claim 4, line 2, please insert -- can -- after "each".

Signed and Sealed this

Ninth Day of June, 2009

JOHN DOLL
*Acting Director of the United States Patent and Trademark Office*